(12) United States Patent
Sueta et al.

(10) Patent No.: US 11,821,007 B2
(45) Date of Patent: *Nov. 21, 2023

(54) METHOD FOR INDUCING DIFFERENTIATION OF INTERMEDIATE MESODERMAL CELL TO RENAL PROGENITOR CELL, AND METHOD FOR INDUCING DIFFERENTIATION OF PLURIPOTENT STEM CELL TO RENAL PROGENITOR CELL

(71) Applicant: KYOTO UNIVERSITY, Kyoto (JP)

(72) Inventors: Shinichi Sueta, Kyoto (JP); Tomoko Kasahara, Kyoto (JP); Kenji Osafune, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 490 days.

This patent is subject to a terminal disclaimer.

(21) Appl. No.: 16/616,942

(22) PCT Filed: May 23, 2018

(86) PCT No.: PCT/JP2018/019886
§ 371 (c)(1),
(2) Date: Nov. 25, 2019

(87) PCT Pub. No.: WO2018/216743
PCT Pub. Date: Nov. 29, 2018

(65) Prior Publication Data
US 2020/0248148 A1 Aug. 6, 2020

(30) Foreign Application Priority Data
May 25, 2017 (JP) ................. 2017-104021

(51) Int. Cl.
C12N 5/071 (2010.01)
C12N 5/074 (2010.01)

(52) U.S. Cl.
CPC ......... *C12N 5/0687* (2013.01); *C12N 5/0696* (2013.01); *C12N 2501/115* (2013.01); *C12N 2501/119* (2013.01); *C12N 2501/155* (2013.01); *C12N 2501/998* (2013.01); *C12N 2533/52* (2013.01)

(58) Field of Classification Search
CPC ................ C12N 5/0687; C12N 5/0696; C12N 2501/115; C12N 2501/119; C12N 2501/155; C12N 2501/998; C12N 2533/52
See application file for complete search history.

(56) References Cited

U.S. PATENT DOCUMENTS

2014/0363888 A1 12/2014 Osafune
2016/0137985 A1* 5/2016 Osafune ................. A61K 35/22
435/377
2016/0237409 A1 8/2016 Little
2016/0304838 A1 10/2016 Nishinakamura
2018/0273905 A1 9/2018 Kawamoto

FOREIGN PATENT DOCUMENTS

| JP | 2015-500630 A | 1/2015 |
| JP | 2016-527878 A | 9/2016 |
| WO | WO 2014/200115 A1 | 12/2014 |
| WO | WO 2015/056756 A1 | 4/2015 |
| WO | WO 2016/094948 A1 | 6/2016 |
| WO | WO 2017/043666 A1 | 3/2017 |
| WO | WO 2017/049243 A1 | 3/2017 |

OTHER PUBLICATIONS

Taguchi et al., Redefining the in vivo origin of metanephric nephron progenitors of complex kidney structures from pluripotent stem cells. Cell Stem Cell, vol. 14, No. 1 (Jan. 2, 2014) pp. 53-67 (Year: 2014).*
Kobayashi, A., et al., Six2 Defines and Regulates a Multipotent Self-Renewing Nephron Progenitor Population throughout Mammalian Kidney Development, Cell Stem Cell, vol. 3, pp. 169-181, 2008.
Morizane, R., et al., Nephron organoids derived from human pluripotent stem cells model kidney development and injury, Nature Biotechnology, vol. 33, No. 11, pp. 1193-1200 (plus Supplementary Information in 2 pages), 2015.
Osafune, K., et al., Identification of multipotent progenitors in the embryonic mouse kidney by a novel colony-forming assay, Development, vol. 133, pp. 151-161, 2005.
Taguchi, A., et al., Redefining the In Vivo Origin of Metanephric Nephron Progenitors Enables Generation of Complex Kidney Structures from Pluripotent Stem Cells, Cell Stem Cell, vol. 14, pp. 53-67, 2014.
Takasato, M., et al., A strategy for generating kidney organoids: Recapitulating the development in human pluripotent stem cells, Developmental Biology, vol. 420, pp. 210-220, 2016.
Takasoto, M., et al., Directing human embryonic stem cell differentiation towards a renal lineage generates a self-organizing kidney, Nature Cell Biology, vol. 16, No. 1, pp. 118-126 (plus Methods and Supplementary Information in 9 pages), 2014.

(Continued)

Primary Examiner — Kara D Johnson
(74) Attorney, Agent, or Firm — Knobbe, Martens, Olson & Bear LLP

(57) ABSTRACT

A method of producing renal progenitor cells from pluripotent stem cells involves culturing pluripotent stem cells in a medium containing FGF2, BMP4, a GSK-3β inhibitor, and retinoic acid or a derivative thereof, culturing the resulting cells in a medium containing FGF2, a GSK-3β inhibitor, and BMP7, culturing the resulting cells in a medium containing FGF2, a GSK-3β inhibitor, BMP7, and a TGFβ inhibitor, culturing the resulting cells in a medium containing FGF2, a GSK-3β inhibitor, BMP7, activin, and a ROCK (Rho-kinase) inhibitor, culturing the resulting cells in a medium containing retinoic acid or a derivative thereof, and FGF9, and culturing the resulting cells in a medium containing a GSK-3β inhibitor and FGF9, to induce renal progenitor cells from intermediate mesodermal cells.

21 Claims, 3 Drawing Sheets

(56) References Cited

OTHER PUBLICATIONS

Takasoto, M., et el., Kidney organoids from human iPS cells contain multiple lineages and model human nephrogenesis, Nature, vol. 526, pp. 564-568 (plus Supplementary Information in 17 pages), 2015.
Toyohara, T., et al., Cell Therapy Using Human Induced Pluripotent Stem Cell-Derived Renal Progenitors Ameliorates Acute Kidney Injury in Mice, Stem Cells Translational Medicine, vol. 4, pp. 980-992, 2015.
International Search Report, dated Aug. 28, 2018, for International Application No. PCT/JP2018/019886.
International Preliminary Report on Patentability, dated Nov. 26, 2019, in International Application No. PCT/JP2018/019886.
Takasato, M., et al., Generation of kidney organoids from human pluripotent stem cells, Nature Protocols, vol. 11, No. 9, pp. 1681-1692, 2016.
Extended European Search Report dated Feb. 9, 2021 in EP Application No. 18805330.0.

* cited by examiner

Bright field image of kidney organoid (nephron-like structure)

Immunostaining image of kidney organoid white (Podocalyxin, glomerulus) red (Lotus tetragonolobus lectin (LTL), proximal renal tubule) green (CDH1, distal renal tubule)

Immunostaining image of kidney organoid white (CDH1) red (Dolichos Biflorus agglutinin (DBA)) green (BRN1) BRN1(+) CDH1(+) DBA(-) Henle's loop

METHOD FOR INDUCING DIFFERENTIATION OF INTERMEDIATE MESODERMAL CELL TO RENAL PROGENITOR CELL, AND METHOD FOR INDUCING DIFFERENTIATION OF PLURIPOTENT STEM CELL TO RENAL PROGENITOR CELL

PRIORITY AND CROSS REFERENCE TO RELATED APPLICATIONS

This application is the U.S. National Stage Application under 35 U.S.C. § 371 of International Application No. PCT/JP2018/019886, filed May 23, 2018, designating the U.S. and published as WO 2018/216743 A1 on Nov. 29, 2018, which claims the benefit of Japanese Patent Application No. JP 2017-104021, filed May 25, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a method of differentiation induction from intermediate mesodermal cells into renal progenitor cells. The present invention also relates to a method of differentiation induction from pluripotent stem cells into renal progenitor cells.

BACKGROUND ART

The number of patients with chronic kidney diseases (CKDs) in Japan is estimated to be about 13 million at present, and these diseases are called a new national disease. Only a limited number of curative treatment methods are available for chronic kidney diseases, and there are not less than 300,000 patients with end-stage chronic renal failure who require dialysis treatment because of progression of the diseases. This has been a serious problem not only from the medical point of view, but also from the viewpoint of medical economy. An example of the curative treatment for chronic kidney diseases, including end-stage chronic renal failure, is kidney transplantation. However, since supply of donor organs is seriously insufficient, their demand has not been satisfied at all.

The kidney is derived from the intermediate mesoderm, which is a tissue in the early fetal period. In vertebrates, three kidneys, that is, the pronephros, the mesonephros, and the metanephros are formed from the intermediate mesoderm, and, in mammals, the metanephros becomes the adult kidney. The metanephros develops as a result of interaction between a tissue called mesenchyme, which differentiates into nephrons and stroma of the adult kidney in the future, and a tissue called ureteric bud, which differentiates into the collecting tubule and, at the position lower than this, the renal pelvis in the adult kidney, the ureter, and part of the bladder in the future. It has also been shown that nephron progenitor cells, which have pluripotency that leads to differentiation into the glomerulus and several kinds of tubular epithelial cells constituting the nephron, are present in the metanephric mesenchyme (Non-patent Documents 1 and 2).

If an efficient method of inducing differentiation from human induced pluripotent stem (iPS) cells or human embryonic stem (ES) cells into nephron progenitor cells is established, it can be expected to be useful, in the future, for three-dimensional reconstruction of a kidney as a solution to the insufficiency of donors in kidney transplantation, and for providing sources of glomeruli and tubular cells in cell therapy. Furthermore, it can be expected to lead to development of assay systems for nephrotoxicity of agents, which systems use glomeruli and tubular cells, and kidney tissues containing these; preparation of disease models using kidney cells and kidney tissues prepared from disease-specific iPS cells; and studies such as development of therapeutic agents.

Although several methods of inducing differentiation from human iPS cells or human ES cells into nephron progenitor cells have been reported (Non-patent Documents 3 to 6), they have problems in that the differentiation induction efficiency is low because of use of an embryoid body (EB) (Non-patent Document 3), and that whether or not each stage of development is accurately reproduced is unclear (Non-patent Documents 4 to 6).

Furthermore, although the group of the present inventors disclosed a method of producing renal progenitor cells from intermediate mesodermal cells, the method comprising a step of culturing intermediate mesodermal cells in a medium containing a TFGβ signal stimulator and a BMP inhibitor (Patent Document 1), there has been a demand for a method which enables more efficient differentiation induction into renal progenitor cells.

PRIOR ART DOCUMENTS

Patent Document

Patent Document 1: WO 2014/200115

Non-Patent Documents

Non-patent Document 1: Osafune K., et al., Development 2006; 133: 151-61.
Non-patent Document 2: Kobayashi A., et al., Cell Stem Cell 2008; 3: 169-81.
Non-patent Document 3: Taguchi A., et al., Cell Stem Cell. 2014; 14: 53-67.
Non-patent Document 4: Takasato M., et al., Nat Cell Biol. 2014; 16: 118-26.
Non-patent Document 5: Takasato M., et al., Nature. 2015; 526: 564-568.
Non-patent Document 6: Morizane R., et al., Nat. Biotechnol. 2015; 33: 1193-1200.

SUMMARY

An object of the present invention is to provide a method of efficiently inducing differentiation from intermediate mesodermal cells into renal progenitor cells. More specifically, an object of the present invention is to provide a method of inducing differentiation from intermediate mesodermal cell into renal progenitor cells, the method comprising subjecting intermediate mesodermal cells induced from pluripotent stem cells further to differentiation induction into renal progenitor cells.

In order to solve the above problems, the present inventors intensively studied and found that differentiation induction from intermediate mesodermal cells into renal progenitor cells is possible by carrying out adherent culture in a medium containing a GSK-3β inhibitor and FGF9. The present invention was completed based on such findings.

More specifically, the present invention has the following characteristics.

[1] A method of producing renal progenitor cells, comprising performing adherent culture of intermediate mesodermal cells in a medium containing a GSK (glycogen synthase kinase)-3β inhibitor and FGF (fibroblast growth factor) 9, to induce renal progenitor cells from intermediate mesodermal cells.

[2] The method according to [1], wherein the renal progenitor cells are SIX2-positive cells.

[3] The method according to [1] or [2], wherein the intermediate mesodermal cells are OSR1-positive cells.

[4] The method according to any one of [1] to [3], wherein the GSK-3β inhibitor is CHIR99021.

[5] The method according to any one of [1] to [4], wherein the medium further contains a ROCK inhibitor.

[6] The method according to any one of [1] to [5], wherein the adherent culture is carried out using a culture vessel coated with an extracellular matrix.

[7] The method according to [6], wherein the extracellular matrix is laminin 511 E8 fragment.

[8] The method according to any one of [1] to [7], wherein the intermediate mesodermal cells are intermediate mesodermal cells induced from pluripotent stem cells.

[9] The method according to [8], wherein the intermediate mesodermal cells are intermediate mesodermal cells produced by a method comprising the following Steps (i) to (v):
   (i) a step of culturing pluripotent stem cells in a medium containing FGF2, BMP (bone morphogenetic protein) 4, a GSK-3β inhibitor, and retinoic acid or a derivative thereof;
   (ii) a step of culturing cells obtained in Step (i) in a medium containing FGF2, a GSK-3β inhibitor, and BMP7;
   (iii) a step of culturing cells obtained in Step (ii) in a medium containing FGF2, a GSK-3β inhibitor, BMP7, and a TGFβ inhibitor;
   (iv) a step of culturing cells obtained in Step (iii) in a medium containing FGF2, a GSK-3β inhibitor, BMP7, activin, and a ROCK inhibitor; and
   (v) a step of culturing cells obtained in Step (iv) in a medium containing retinoic acid or a derivative thereof, and FGF9.

[10] The method according to [9], wherein the medium in Step (v) further contains a BMP inhibitor.

[11] The method according to [8] or [10], wherein the pluripotent stem cells are induced pluripotent stem (iPS) cells.

[12] The method according to [11], wherein the iPS cells are human iPS cells.

[13] A method of producing renal progenitor cells from pluripotent stem cells, the method comprising the following Steps (i) to (vi):
   (i) a step of culturing pluripotent stem cells in a medium containing FGF2, BMP4, a GSK-3β inhibitor, and retinoic acid or a derivative thereof;
   (ii) a step of culturing cells obtained in Step (i) in a medium containing FGF2, a GSK-3β inhibitor, and BMP7;
   (iii) a step of culturing cells obtained in Step (ii) in a medium containing FGF2, a GSK-3β inhibitor, BMP7, and a TGFβ inhibitor;
   (iv) a step of culturing cells obtained in Step (iii) in a medium containing FGF2, a GSK-3β inhibitor, BMP7, activin, and a ROCK (Rho-kinase) inhibitor;
   (v) a step of culturing cells obtained in Step (iv) in a medium containing retinoic acid or a derivative thereof, and FGF9; and
   (vi) a step of culturing cells obtained in Step (v) in a medium containing a GSK-3β inhibitor and FGF9, to induce renal progenitor cells from intermediate mesodermal cells.

[14] The method according to [13], wherein the medium in Step (v) further contains a BMP inhibitor.

[15] The method according to [13] or [14], wherein the renal progenitor cells are SIX2-positive cells.

[16] The method according to any one of [13] to [15], wherein the cells obtained in Step (v) are OSR1-positive cells.

[17] The method according to any one of [13] to [16], wherein the GSK-3β inhibitor is CHIR99021.

[18] The method according to any one of [13] to [17], wherein the medium in Step (vi) further contains a ROCK inhibitor.

[19] The method according to any one of [13] to [18], wherein the culture is carried out using a culture vessel coated with an extracellular matrix.

[20] The method according to [19], wherein the extracellular matrix is laminin 511 E8 fragment.

[21] The method according to any one of [13] to [20], wherein the pluripotent stem cells are induced pluripotent stem (iPS) cells.

[22] The method according to [21], wherein the iPS cells are human iPS cells.

[23] A renal progenitor cell produced by the method according to any one of [1] to [22].

[24] A kidney organoid obtained using a renal progenitor cell produced by the method according to any one of [1] to [22].

[25] A pharmaceutical composition comprising: a renal progenitor cell produced by the method according to any one of [1] to [22]; or a kidney organoid obtained using the renal progenitor cell.

[26] A therapeutic agent for a kidney disease, comprising: a renal progenitor cell produced by the method according to any one of [1] to [22]; or a kidney organoid obtained using the renal progenitor cell.

According to the method of the present invention, culture can be performed by adherent culture. Therefore, differentiation induction from human iPS cells into renal progenitor cells is possible with an efficiency of as high as not less than 80%. Further, since the method accurately reproduces the developmental differentiation stages of the posterior epiblast, late somite mesodermal cells, and posterior intermediate mesodermal cells, from which metanephric mesenchyme nephron progenitor cells are derived, analysis of the cells in each stage is also possible.

The metanephros is a fetal kidney tissue that forms the adult kidney, and is an indispensable component for kidney regeneration. Further, since many kidney diseases occur in metanephric nephron progenitor cells, and glomeruli and renal tubules derived therefrom, the method of the present invention is useful also for preparation of kidney disease models. Thus, the method of the present invention is useful also from the viewpoint of searching for therapeutic methods and therapeutic agents for kidney diseases.

DETAILED DESCRIPTION

Figure 1:
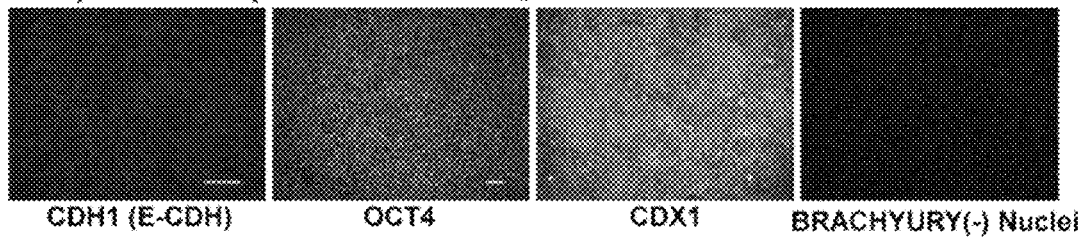
FIG. 1 shows a diagram (photographs) showing results of immunocytostaining that shows a late posterior epiblast, a mesodermal-lineage late primitive streak, a metanephric-lineage late primitive streak, a late posterior intermediate mesoderm, and nephron progenitor cells (renal progenitor cells) induced by differentiation from human iPS cells. For the late posterior intermediate mesoderm and the nephron progenitor cells, the ratios of marker-positive cells according to FACS are also shown.
Figure 1:
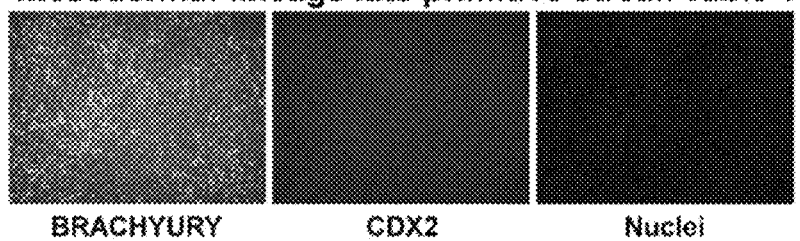
Figure 1:
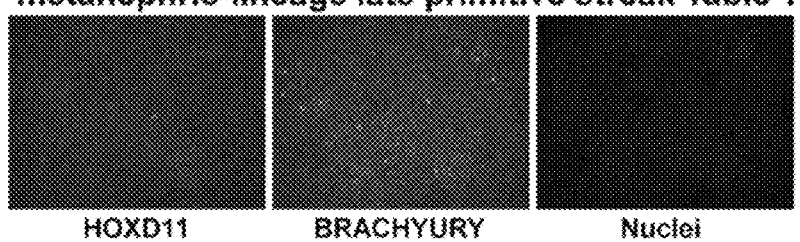
Figure 1:
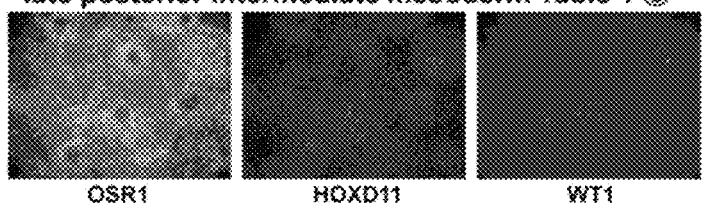
Figure 1:
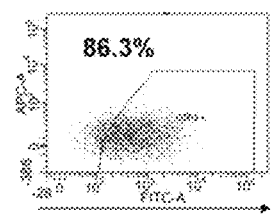
Figure 1:
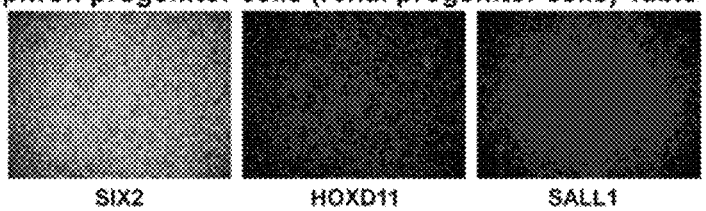
Figure 1:
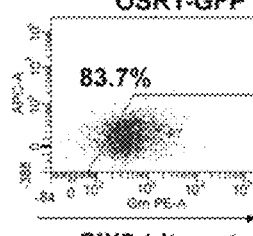

The present invention is described below in detail.
<Differentiation Induction from Intermediate Mesodermal Cells into Renal Progenitor Cells>

The present invention provides a method of producing renal progenitor cells, comprising culturing intermediate mesodermal cells in a medium containing a GSK-3β inhibitor and FGF9 (also referred to as renal progenitor cell differentiation induction step).

In the present invention, intermediate mesodermal cells mean arbitrary cells that are induced into renal progenitor cells by culture in a medium containing a GSK-3β inhibitor and FGF9. Examples of known methods of obtaining intermediate mesodermal cells include methods by differentiation induction from mouse or human pluripotent stem cells into intermediate mesodermal cells (Biochem Biophys Res Commun. 393: 877-82 (2010); Nat Commun. 4: 1367 (2013); WO 2012/011610; and Patent Document 1). As a marker that characterizes intermediate mesodermal cells, OSR1 is known. Examples of the intermediate mesodermal cells used in the method of the present invention include OSR1-positive intermediate mesodermal cells. For example, pluripotent stem cells having a reporter gene (such as GFP) introduced therein such that the gene is regulated by the OSR1 promoter (for example, the OSR1-GFP reporter human iPS cells described in the later-mentioned Examples) may be cultured, and then OSR1-positive intermediate mesodermal cells may be isolated by a method known in the art (such as a method using a cell sorter) using expression of the reporter gene as an index. Further, expression of OSR1 in intermediate mesodermal cells may be confirmed by a method by analysis of gene expression such as quantitative RT-PCR (Nat Commun 4, 1367, (2013)). In the present invention, examples of the OSR1-positive intermediate mesodermal cells include cells expressing OSR1 protein, and cells expressing a protein encoded by a gene regulated by the OSR1 promoter. In the present invention, examples of the OSR1 include genes having the nucleotide sequence of the NCBI accession No. NM_145260.2 in cases of human, or NM_011859.3 in cases of mouse; proteins encoded by these genes; and naturally occurring variants having their functions. Preferably, the intermediate mesodermal cells used in the method of the present invention are cells negative for SIX2, and positive for OSR1, HOX11, and WT1.

In the present invention, renal progenitor cells are regarded as cells equivalent to nephron progenitor cells. They are cells capable of differentiation in vitro into organ structures such as a glomerulus-like structure or a renal tubule-like structure. The differentiation capacity into organ structures can be evaluated by, for example, a method described in Osafune K, et al. (2006), Development 133: 151-61. As a characteristic factor for maintenance of the state as a renal progenitor cell, SIX2 is known (Cell Stem Cell 3: 169-181 (2008)). Examples of the renal progenitor cells induced by the method of the present invention include SIX2-positive renal progenitor cells. For example, pluripotent stem cells having a reporter gene (such as tdTomato) introduced therein such that the gene is regulated by the SIX2 promoter (for example, the OSR1-GFP/SIX2-tdTomato reporter human iPS cells described in the later-mentioned Examples) may be cultured, and then SIX2-positive renal progenitor cells may be isolated by a method known in the art (such as a method using a cell sorter) using expression of the reporter gene as an index. Further, expression of SIX2 in renal progenitor cells may be confirmed by a method by analysis of gene expression such as quantitative RT-PCR (Nat Commun 4, 1367, (2013)). In the present invention, examples of the SIX2-positive renal progenitor cells include cells expressing SIX2 protein, and cells expressing a protein encoded by a gene regulated by the SIX2 promoter. In the present invention, examples of the SIX2 include genes having the nucleotide sequence of the NCBI accession No. NM_016932.4 in cases of human, or NM_011380.2 in cases of mouse; proteins encoded by these genes; and naturally occurring variants having their functions. Preferably, the renal progenitor cells induced by the method of the present invention are cells positive for OSR1, and also positive for HOX11, WT1, SIX2, and SALL1.

In the present invention, the intermediate mesodermal cells or the renal progenitor cells may be provided as a cell population containing another type of cells, or may be a purified population. The cell population is preferably a cell population containing the corresponding cells at not less than 5%, not less than 6%, not less than 7%, not less than 8%, not less than 9%, 10%, 20%, 28%, or not less than 30%. The purification may be carried out by a method such as FACS using the above markers as indices.

In the present invention, the adherent culture means that cells are cultured in a state where the cells adhere to a culture substrate, for example, in a culture dish subjected to coating treatment. The coating agent is preferably an extracellular matrix, and examples thereof include substances such as collagen, proteoglycan, fibronectin, hyaluronic acid, tenascin, entactin, elastin, fibrillin, and laminin, and fragments thereof. These extracellular matrices may be used in combination as, for example, a product prepared from cells such as BD Matrigel (trademark). The extracellular matrix is preferably laminin or a fragment thereof. In the present invention, laminin is a protein having a heterotrimer structure having one α chain, one β chain, and one γ chain. The protein is an extracellular matrix protein having isoforms with different compositions of the subunit chains. Laminin has about 15 kinds of isoforms in which the heterotrimer has combinations of 5 kinds of α chains, 4 kinds of β chains, and 3 kinds of γ chains. For example, the α chain may be α1, α2, α3, α4, or α5; the β chain may be β1, β2, β3, or β4; and the γ chain may be γ1, γ2, or γ3; although these chains are not limited thereto. The laminin is more preferably laminin 511, which is composed of α5, β1, and γ1 (Nat Biotechnol 28, 611-615 (2010)). The laminin may also be a fragment, and the fragment is not limited as long as it has integrin-binding activity. For example, the fragment may be E8 fragment (laminin 511E8), which is a fragment obtained by digestion with elastase (EMBO J., 3:1463-1468, 1984; J. Cell Biol., 105: 589-598, 1987; WO 2011/043405). Laminin 511E8 is commercially available, and can be purchased from, for example, Nippi, Inc.

The medium for the renal progenitor cell differentiation induction step may be prepared by adding a GSK-3β inhibitor and FGF9 to a basal medium for use in animal cell culture. Examples of the basal medium include IMDM, Medium 199, Eagle's Minimum Essential Medium (EMEM), αMEM, Dulbecco's modified Eagle's Medium (DMEM), Ham's F12 (F12) medium, RPMI 1640 medium, Fischer's medium, and mixed media thereof. The medium may contain serum (for example, fetal bovine serum (FBS)), or may be serum-free. When necessary, the medium may contain one or more of serum replacements such as albumin, transferrin, KnockOut Serum Replacement (KSR) (serum replacement for ES cell culture) (Invitrogen), N2 supplement (Invitrogen), B27 supplement (Invitrogen), fatty acids, insulin, collagen precursor, trace elements, 2-mercaptoethanol, and 3'-thiolglycerol, and may also contain one or more of substances such as lipids, amino acids, L-glutamine, GlutaMAX (Invitrogen), non-essential amino acids (NEAA), vitamins, growth factors, antibiotics, antioxidants, pyruvic acid, buffers, inorganic salts, and equivalents thereof. Media preliminarily optimized for stem cell culture, such as ReproFF2 (ReproCELL), may also be used. The medium for the renal progenitor cell differentiation induction step may also contain a ROCK inhibitor such as Y-27632 as mentioned later.

The GSK-3β inhibitor to be used in the renal progenitor cell differentiation induction step is not limited as long as it is capable of inhibiting a function of GSK-3β such as kinase activity. Examples of the GSK-3β inhibitor include BIO (another name, GSK-3β inhibitor IX; 6-bromoindirubin-3'-oxime), which is an indirubin derivative; SB216763 (3-(2, 4-dichlorophenyl)-4-(1-methyl-1H-indol-3-yl)-1H-pyrrole-2,5-dione), which is a maleimide derivative; GSK-3β inhibitor VII (α,4-dibromoacetophenone), which is a phenyl-α-bromomethyl ketone compound; L803-mts (another name, GSK-3β peptide inhibitor; Myr-N-GKEAP-PAPPQSpP-NH$_2$), which is a cell membrane-permeable phosphorylated peptide; and CHIR99021, which has high selectivity (Nature (2008) 453: 519-523). These compounds are available from, for example, Stemgent, Calbiochem, and Biomol, and may also be prepared. A preferred example of the GSK-3β inhibitor used in the present step is CHIR99021. The concentration of the GSK-3β inhibitor to be used in the present step can be appropriately selected by those skilled in the art depending on the GSK-3β inhibitor used, and is, for example, 0.01 μM to 100 μM, preferably 0.1 μM to 10 μM, more preferably 0.5 μM to 3 μM, especially preferably 0.5 μM to 1.5 μM.

The FGF9 to be used in the renal progenitor cell differentiation induction step is preferably human FGF9, and examples of the human FGF9 include a protein having the amino acid sequence of the NCBI (National Center for Biotechnology Information) accession No. NP_002001.1. The FGF9 also includes fragments and functionally modified products thereof as long as they have differentiation induction activity. As the FGF9, a commercially available product may be used, or a protein purified from cells or a protein produced by genetic recombination may be used. The concentration of the FGF9 to be used in this step is, for example, 1 ng/ml to 500 ng/ml, 1 ng/ml to 100 ng/ml, 5 ng/ml to 50 ng/ml, or 5 ng/ml to 25 ng/ml There is no upper limit of the number of days of culture in the renal progenitor cell differentiation induction step since long-term culture does not affect the production efficiency of the renal progenitor cells. The number of days is, for example, not less than 2 days, not less than 3 days, not less than 4 days, or not less than 5 days. In the renal progenitor cell differentiation induction step, the culture temperature is not limited, and may be about 30 to 40° C., preferably about 37° C. The culture is carried out in an atmosphere of $CO_2$-containing air wherein the $CO_2$ concentration is preferably about 2 to 5%.

In one embodiment of the present invention, the intermediate mesodermal cells are intermediate mesodermal cells induced from pluripotent stem cells. In such cases, the induced intermediate mesodermal cells may be once isolated, and then the isolated intermediate mesodermal cells may be induced into renal progenitor cells by the culture step in the present invention. Alternatively, after the induction of the intermediate mesodermal cells from the pluripotent stem cells, the intermediate mesodermal cells may be subjected, without isolation, to the culture step in the present invention to induce renal progenitor cells.

In cases where the intermediate mesodermal cells are isolated, pluripotent stem cells having a reporter gene whose expression is regulated by the endogenous OSR1 promoter may be used. Examples of methods of introducing a reporter gene into pluripotent stem cells such that the gene is regulated by the OSR1 promoter include homologous recombination using a BAC vector or the like as described in, for example, WO 2012/011610. For the isolation of the induced renal progenitor cells, pluripotent stem cells having a reporter gene whose expression is regulated by the SIX2 promoter may also be used. Such cells can be prepared by the same method as described above. Examples of the reporter gene include genes encoding known reporter proteins such as β-galactosidase, β-glucuronidase, luciferase, green fluorescent protein (GFP), tdTomato, and cell surface protein. The intermediate mesodermal cells or the renal progenitor cells induced from these pluripotent stem cells can be isolated using a method known in the art, such as a method that uses a cell sorter using, as an index, expression of the reporter protein, a method in which cells are sorted based on magnetism using magnetic beads together with an antibody against the cell surface protein (for example, MACS), or a method that uses a carrier to which the antibody or the like is immobilized (for example, a cell enrichment column).

In the present invention, the pluripotent stem cells are stem cells having pluripotency that allows differentiation into many kinds of cells present in a living body, which stem cells also have the growth ability. The pluripotent stem cells include arbitrary cells which can be induced into the intermediate mesodermal cells used in the present invention. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells). The pluripotent stem cells are preferably iPS cells from the viewpoint of the fact that these cells can be obtained without destroying embryos, eggs, or the like during the production process. The pluripotent stem cells are more preferably human iPS cells.

Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used either individually or in combination. Examples of the combinations of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26: 2467-2474; Huangfu D, et al. (2008), Nat. Biotechnol. 26: 1269-1275; Shi Y, et al. (2008), Cell Stem Cell, 3, 568-574; Zhao Y, et al. (2008), Cell Stem Cell, 3: 475-479; Marson A, (2008), Cell Stem Cell, 3, 132-135; Feng B, et al. (2009), Nat. Cell Biol. 11: 197-203; R. L. Judson et al., (2009), Nat. Biotechnol., 27: 459-461; Lyssiotis C A, et al. (2009), Proc Natl Acad Sci USA. 106: 8912-8917; Kim J B, et al. (2009), Nature. 461: 649-643; Ichida J K, et al. (2009), Cell Stem Cell. 5: 491-503; Heng J C, et al. (2010), Cell Stem Cell. 6: 167-74; Han J, et al. (2010), Nature. 463: 1096-100; Mali P, et al. (2010), Stem Cells. 28: 713-720; and Maekawa M, et al. (2011), Nature. 474: 225-9.

Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include: (1) tissue stem cells (somatic stem cells) such as neural stem cells, hematopoietic stem cells, mesenchymal stem cells, and dental pulp stem cells; (2) tissue progenitor cells; and (3) differentiated cells such as blood cells (peripheral blood cells, cord blood cells, and the like), lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In cases where iPS cells are used as a material of the cells to be transplanted, somatic cells whose HLA genotype is the same or substantially the same as that of the individual to which the cells are to be transplanted are preferably used in view of prevention of the rejection reaction. The term "substantially the same" herein means that the HLA genotype is matching to an extent at which the immune reaction against the transplanted cells can be suppressed with an immunosuppressive agent. For example, the somatic cells have matched HLA types at the three loci HLA-A, HLA-B, and HLA-DR, or at the four loci further including HLA-C.

<Differentiation Induction from Pluripotent Stem Cells into Intermediate Mesodermal Cells>

In the present invention, for the differentiation induction from pluripotent stem cells into intermediate mesodermal cells, a method including the following steps may be used.

(i) A step of culturing pluripotent stem cells in a medium containing FGF2, BMP (bone morphogenetic protein) 4, a GSK-3β inhibitor, and retinoic acid or a derivative thereof;

(ii) a step of culturing cells obtained in Step (i) in a medium containing FGF2, a GSK-3β inhibitor, and BMP7;

(iii) a step of culturing cells obtained in Step (ii) in a medium containing FGF2, a GSK-3β inhibitor, BMP7, and a TGFβ inhibitor;

(iv) a step of culturing cells obtained in Step (iii) in a medium containing FGF2, a GSK-3β inhibitor, BMP7, activin, and a ROCK inhibitor; and (v) a step of culturing cells obtained in Step (iv) in a medium containing retinoic acid or a derivative thereof, and FGF9.

Each step is further described below.

(i) Step of Culturing Pluripotent Stem Cells in Medium Containing FGF2, BMP4, GSK-3β Inhibitor, and Retinoic Acid or Derivative Thereof In this step, a late posterior epiblast is induced from pluripotent stem cells. The late posterior epiblast is characterized as cells positive for at least one of the markers CDX1, OCT4, NANOG, and E-CDH (CDH1), preferably cells positive for all of these markers. Further, the late posterior epiblast is preferably negative for EOMES and BRACHYURY.

In Step (i), pluripotent stem cells are separated by an arbitrary method known in the art, and cultured preferably by adherent culture.

Examples of the method of separating the pluripotent stem cells include mechanical separation; and separation using a separation solution having protease activity and collagenase activity (for example, Accutase™ or Accumax™ (Innovative Cell Technologies, Inc.)) or a separation solution having only collagenase activity. The method is preferably a method in which the cells are dissociated using a separation solution having protease activity and collagenase activity, and then mechanically finely dispersed into single cells. As the human pluripotent stem cells used in Step (i), colonies cultured to 70% to 80% confluence with respect to the dish used are preferably used.

The medium to be used in Step (i) may be prepared by adding FGF2, BMP4, a GSK-3β inhibitor, and retinoic acid or a derivative thereof to a basal medium for use in animal cell culture. As the basal medium, the above-described basal media may be used. The medium may contain serum, or may be serum-free. When necessary, the medium may also contain a serum replacement, lipid, amino acid, vitamin, growth factor, low molecular weight compound, antibiotic, antioxidant, pyruvic acid, buffer, inorganic salt, or the like.

As the GSK-3β inhibitor to be used in Step (i), the GSK-3β inhibitors exemplified above for the renal progenitor cell differentiation induction step may be used. A preferred example of the GSK-3β inhibitor is CHIR99021. The concentration of the GSK-3β inhibitor used in Step (i) can be appropriately selected by those skilled in the art depending on the GSK-3β inhibitor used, and is, for example, 0.01 µM to 100 µM, preferably 0.1 µM to 10 µM, more preferably 0.5 µM to 3 µM, especially preferably 0.5 µM to 1.5 µM.

The FGF2 (basic FGF: bFGF) to be used in Step (i) is preferably human FGF2, and examples of the human FGF2 include protein having the amino acid sequence of the NCBI (National Center for Biotechnology Information) accession No. ABO43041.1. The FGF2 also includes fragments and functionally modified products thereof as long as they have differentiation induction activity. As the FGF2, a commercially available product may be used, or a protein purified from cells or a protein produced by genetic recombination may be used. The concentration of the FGF2 to be used in this step is 1 ng/ml to 1000 ng/ml, preferably 10 ng/ml to 500 ng/ml, more preferably 50 ng/ml to 250 ng/ml.

The BMP4 used in Step (i) is preferably human BMP4, and examples of the human BMP4 include protein having the amino acid sequence of the NCBI (National Center for Biotechnology Information) accession No. AAH20546.1. The BMP4 also includes fragments and functionally modified products thereof as long as they have differentiation induction activity. As the BMP4, a commercially available product may be used, or a protein purified from cells or a protein produced by genetic recombination may be used. The concentration of the BMP4 to be used in this step is 0.1 ng/ml to 100 ng/ml, preferably 0.5 ng/ml to 50 ng/ml, more preferably 0.5 ng/ml to 5 ng/ml.

The retinoic acid used in Step (i) may be retinoic acid itself, or may be a retinoic acid derivative retaining the differentiation induction function of naturally occurring retinoic acid. Examples of the retinoic acid derivative include 3-dehydroretinoic acid; 4-[[(5,6,7,8-tetrahydro-5,5,8,8-tetramethyl-2-naphthalenyl)carbonyl]amino]-benzoic acid (AM580) (Tamura K, et al., Cell Differ. Dev. 32: 17-26 (1990)); 4-[(1E)-2-(5,6,7,8-tetrahydro-5,5,8,8-tetramethyl-2-naphthalenyl)-1-propen-1-yl]-benzoic acid (TTNPB) (Strickland S, et al., Cancer Res. 43: 5268-5272 (1983)); a compound described in Tanenaga, K. et al., Cancer Res. 40: 914-919 (1980); retinol palmitate; retinol; retinal; 3-dehydroretinol; and 3-dehydroretinal.

The concentration of the retinoic acid or the derivative thereof to be used in Step (i) is, for example, 1 nM to 100 nM, preferably 5 nM to 50 nM, more preferably 5 nM to 25 nM.

In Step (i), the culture temperature is not limited, and may be about 30 to 40° C., preferably about 37° C. The culture is carried out in an atmosphere of $CO_2$-containing air. The $CO_2$ concentration is about 2 to 5%, preferably about 5%. The culture period in Step (i) is not limited as long as it is a period sufficient for differentiation induction into the late posterior epiblast. The culture is carried out for, for example, 1 or 2 days, preferably 1 day.

(ii) Step of Culturing Cells Obtained in Step (i) in Medium Containing FGF2, GSK-3β Inhibitor, and BMP7

In this step, a mesodermal-lineage primitive streak is induced from a late posterior epiblast. The mesodermal-lineage primitive streak is characterized as cells positive for CDX1 and BRACHYURY. Further, the mesodermal-lineage primitive streak is preferably negative for OCT4, NANOG, and E-CDH.

In Step (ii), a cell population obtained in the Step (i) may be isolated and subjected to adherent culture in a separately provided culture dish that has been subjected to coating treatment. Alternatively, cells obtained by adherent culture in Step (i) may be continuously cultured as they are by replacement of the medium.

The medium to be used in Step (ii) may be prepared by adding FGF2, a GSK-3β inhibitor, and BMP7 to a basal medium for use in animal cell culture. As the basal medium, the above-described basal media may be used. The medium may contain serum, or may be serum-free. When necessary, the medium may also contain a serum replacement, lipid, amino acid, vitamin, growth factor, low molecular weight compound, antibiotic, antioxidant, pyruvic acid, buffer, inorganic salt, or the like.

The FGF2 to be used in Step (ii) and its preferred concentration range are as described for Step (i).

As the GSK-3β inhibitor to be used in Step (ii), the GSK-3β inhibitors exemplified above for Step (i) may be used. A preferred example of the GSK-3β inhibitor is CHIR99021. The concentration of the GSK-3β inhibitor to be used in Step (ii) can be appropriately selected by those skilled in the art depending on the GSK-3β inhibitor used, and is, for example, 0.01 µM to 100 µM, preferably 0.1 µM to 10 µM, more preferably 1 µM to 7.5 µM, especially preferably 2 to 5 µM. The concentration of the GSK-3β inhibitor to be used in Step (ii) is preferably higher than the concentration in Step (i).

The BMP7 to be used in Step (ii) is preferably human BMP7, and examples of the human BMP7 include protein having the amino acid sequence of the NCBI (National Center for Biotechnology Information) accession No. NM_001719.2. The BMP7 also includes fragments and functionally modified products thereof as long as they have differentiation induction activity. As the BMP7, a commercially available product may be used, or a protein purified from cells or a protein produced by genetic recombination may be used. The concentration of the BMP7 to be used in this step is 0.1 ng/ml to 100 ng/ml, preferably 0.5 ng/ml to 50 ng/ml, more preferably 0.5 ng/ml to 5 ng/ml.

In Step (ii), the culture temperature is not limited, and may be about 30 to 40° C., preferably about 37° C. The culture is carried out in an atmosphere of $CO_2$-containing air. The $CO_2$ concentration is about 2 to 5%, preferably about 5%. The culture period in Step (ii) is not limited as long as it is a period sufficient for differentiation induction into the mesodermal-lineage primitive streak. The culture is carried out, for, for example, 10 hours to 2 days, or 1 or 2 days, preferably 0.5 to 1 day.

(iii) Step of Culturing Cells Obtained in Step (ii) in Medium Containing FGF2, GSK-3β Inhibitor, BMP7, and TGFβ Inhibitor In this step, a mesodermal-lineage late primitive streak is induced from a mesodermal-lineage primitive streak. The mesodermal-lineage late primitive streak is characterized as cells positive for CDX2 and BRACHYURY.

In Step (iii), a cell population obtained in the Step (ii) may be isolated and subjected to adherent culture in a separately provided culture dish that has been subjected to coating treatment. Alternatively, cells obtained by adherent culture in Step (ii) may be continuously cultured as they are by replacement of the medium.

The medium to be used in Step (iii) may be prepared by adding FGF2, a GSK-3β inhibitor, BMP7, and a TGFβ inhibitor to a basal medium for use in animal cell culture. As the basal medium, the above-described basal media may be used. The medium may contain serum, or may be serum-free. When necessary, the medium may also contain a serum replacement, lipid, amino acid, vitamin, growth factor, low molecular weight compound, antibiotic, antioxidant, pyruvic acid, buffer, inorganic salt, or the like.

The FGF2, the GSK-3β inhibitor, and the BMP7 to be used in Step (iii), and their preferred concentration ranges are as described for Step (ii). The concentration range of the GSK-3β inhibitor is 0.01 µM to 100 µM, preferably 0.1 µM to 10 µM, more preferably 1 µM to 7.5 µM, especially preferably 2 to 5 µM.

The TGFβ inhibitor to be used in Step (iii) is a substance which inhibits signal transduction that proceeds from binding of TGFβ to its receptor to SMAD. Examples of the TGFβ inhibitor include substances that inhibit binding to the ALK family, which is a receptor, and substances that inhibit phosphorylation of SMAD by the ALK family. Examples of such substances include Lefty-1 (for example, NCBI Accession Nos. NM_010094 (mouse) and NM_020997 (human)); SB431542 and SB202190 (these are described in R. K. Lindemann et al., Mol. Cancer, 2003, 2:20); SB505124 (GlaxoSmithKline); NPC30345, SD093, SD908, and SD208 (Scios); LY2109761, LY364947, and LY580276 (Lilly Research Laboratories); A83-01 (WO 2009146408); and derivatives thereof. The TGFβ inhibitor may be preferably A83-01.

The concentration of the TGFβ inhibitor in the medium is not limited as long as it allows inhibition of ALK, and may be 0.5 μM to 100 μM, preferably 1 μM to 50 μM, more preferably 5 μM to 25 μM.

In Step (iii), the culture temperature is not limited, and may be about 30 to 40° C., preferably about 37° C. The culture is carried out in an atmosphere of $CO_2$-containing air. The $CO_2$ concentration is about 2 to 5%, preferably about 5%. The culture period in Step (iii) is not limited as long as it is a period sufficient for differentiation induction into the mesodermal-lineage late primitive streak. The culture is carried out for, for example, 1 or 3 days, preferably 1.5 to 2 days.

(iv) Step of Culturing Cells Obtained in Step (iii) in Medium Containing FGF2, GSK-3β Inhibitor, BMP7, Activin, and ROCK Inhibitor In this step, a metanephric-lineage late primitive streak is induced from a mesodermal-lineage late primitive streak. The metanephric-lineage late primitive streak is characterized as cells positive for HOX11 and BRACHYURY.

In Step (iv), a cell population obtained in the Step (iii) may be isolated and subjected to adherent culture in a separately provided culture dish that has been subjected to coating treatment. Alternatively, cells obtained by adherent culture in Step (iii) may be continuously cultured as they are by replacement of the medium.

The medium to be used in Step (iv) may be prepared by adding FGF2, a GSK-3β inhibitor, BMP7, activin, and a ROCK inhibitor to a basal medium for use in animal cell culture. As the basal medium, the above-described basal media may be used. The medium may contain serum, or may be serum-free. When necessary, the medium may also contain a serum replacement, lipid, amino acid, vitamin, growth factor, low molecular weight compound, antibiotic, antioxidant, pyruvic acid, buffer, inorganic salt, or the like.

The FGF2, the GSK-3β inhibitor, and the BMP7 used in Step (iv), and their preferred concentration ranges are as described for Step (ii). The concentration range of the GSK-3β inhibitor is 0.01 μM to 100 μM, preferably 0.1 μM to 10 μM, more preferably 1 μM to 7.5 μM, especially preferably 2 to 5 μM.

The activin to be used in Step (iv) includes activins derived from human and other animals, and functionally modified products thereof. For example, commercially available products from R&D Systems and the like may be used. The concentration of the activin to be used in Step (iv) is 1 ng/ml to 100 ng/ml, preferably 5 ng/ml to 50 ng/ml, more preferably 5 ng/ml to 25 ng/ml.

The ROCK inhibitor to be used in Step (iv) is not limited as long as the function of Rho-kinase (ROCK) can be suppressed therewith. Examples of the ROCK inhibitor include Y-27632 (see, for example, Ishizaki et al., Mol. Pharmacol. 57, 976-983 (2000), and Narumiya et al., Methods Enzymol. 325, 273-284 (2000)), Fasudil/HA1077 (see, for example, Uenata et al., Nature 389: 990-994 (1997)), H-1152 (see, for example, Sasaki et al., Pharmacol. Ther. 93: 225-232 (2002)), Wf-536 (see, for example, Nakajima et al., Cancer Chemother Pharmacol. 52(4): 319-324 (2003)), and derivatives thereof; antisense nucleic acids, RNA interference-inducing nucleic acids (for example, siRNAs), and dominant negative mutants against ROCK, and expression vectors therefor. As the ROCK inhibitor, other known low molecular weight compounds may also be used (see, for example, US 2005/0209261 A, US 2005/0192304 A, US 2004/0014755 A, US 2004/0002508 A, US 2004/0002507 A, US 2003/0125344 A, US 2003/0087919 A, WO 2003/062227, WO 2003/059913, WO 2003/062225, WO 2002/076976, and WO 2004/039796). In the present invention, one or more ROCK inhibitors may be used. A preferred example of the ROCK inhibitor is Y-27632. The concentration of the ROCK inhibitor to be used in Step (iv) can be appropriately selected by those skilled in the art depending on the ROCK inhibitor used, and is, for example, 0.1 μM to 100 μM, preferably 1 μM to 75 μM, more preferably 5 μM to 50 μM.

In Step (iv), the culture temperature is not limited, and may be about 30 to 40° C., preferably about 37° C. The culture is carried out in an atmosphere of $CO_2$-containing air. The $CO_2$ concentration is about 2 to 5%, preferably about 5%. The culture period in Step (iv) is not limited as long as it is a period sufficient for differentiation induction into the metanephric-lineage late primitive streak. The culture is carried out for, for example, 1 to 5 days, preferably 3 days.

(v) Step of Culturing Cells Obtained in Step (iv) in Medium Containing Retinoic Acid or Derivative Thereof, and FGF9

In this step, a late posterior intermediate mesoderm is induced from a metanephric-lineage late primitive streak. The intermediate mesoderm is characterized as cells positive for OSR1, HOX11, and WT1.

In Step (v), a cell population obtained in the Step (iv) may be isolated and subjected to adherent culture in a separately provided culture dish that has been subjected to coating treatment. Alternatively, cells obtained by adherent culture in Step (iv) may be continuously cultured as they are by replacement of the medium.

The medium to be used in Step (v) may be prepared by adding retinoic acid or a derivative thereof, and FGF9 to a basal medium for use in animal cell culture. As the basal medium, the above-described basal media may be used. The medium may contain serum, or may be serum-free. When necessary, the medium may also contain a serum replacement, lipid, amino acid, vitamin, growth factor, low molecular weight compound, antibiotic, antioxidant, pyruvic acid, buffer, inorganic salt, or the like.

The retinoic acid or a derivative thereof, and the FGF9 to be used in Step (v), are as described for Step (i) and the renal progenitor cell induction step, respectively, and their preferred concentration ranges are also as described therefor.

The medium used in Step (v) may also contain a BMP inhibitor.

Examples of the BMP inhibitor include protein-based inhibitors such as Chordin, Noggin and Follistatin; Dorsomorphin (that is, 6-[4-(2-piperidin-1-yl-ethoxy)phenyl]-3-pyridin-4-yl-pyrazolo[1,5-a]pyrimidine) and its derivatives (P. B. Yu et al. (2007), Circulation, 116:II_60; P. B. Yu et al. (2008), Nat. Chem. Biol., 4: 33-41; J. Hao et al. (2008), PLoS ONE, 3(8): e2904); and LDN193189 (that is, 4-(6-(4-(piperazin-1-yl)phenyl)pyrazolo[1,5-a]pyrimidin-3-yl) quinoline).

The BMP inhibitor is more preferably NOGGIN, and its concentration may be, for example, 1 to 100 ng/ml.

In Step (v), the culture temperature is not limited, and may be about 30 to 40° C., preferably about 37° C. The culture is carried out in an atmosphere of $CO_2$-containing air. The $CO_2$ concentration is about 2 to 5%, preferably about 5%.

The culture period in Step (v) is not limited as long as it is a period sufficient for differentiation induction into the late posterior intermediate mesoderm. The culture is carried out for, for example, 1 to 3 days, preferably 2 days.

By culturing the intermediate mesodermal cells obtained in Step (v) in a medium containing a GSK-3β inhibitor and FGF9 as described for the renal progenitor cell induction step, renal progenitor cells can be induced.

The present invention also provides a kidney organoid obtained by using a renal progenitor cell produced by the method described above. Kidney organoids from iPS cells are reported in, for example, Nature, 526, 564-568 (2015). In the present invention, the kidney organoid may be obtained by, for example, culturing renal progenitor cells obtained by the above method to prepare a cell cluster, and then co-culturing the cell cluster with feeder cells such as 3T3-Wnt4 cells, with fetal mouse spinal cord cells, or with fetal mouse kidney cells, or subjecting the cell cluster to semi-gas phase culture (reference: Nature, 526, 564-568 (2015)) using a basal medium containing a GSK-3β inhibitor such as CHIR99021. The medium may contain FGF9 or FGF2 in addition to the GSK-3β inhibitor.

The present invention provides a pharmaceutical composition containing a renal progenitor cell obtained by the above method or a kidney organoid obtained using the cell, a therapeutic agent for a kidney disease containing the renal progenitor cell or a kidney organoid obtained using the cell, and a method of treating a kidney disease comprising a step of administering a therapeutically effective amount of the renal progenitor cell or a kidney organoid obtained using the cell. Examples of the method of administering the therapeutic agent to a patient requiring treatment include: a method in which the obtained renal progenitor cells are formed into a sheet, and the sheet is attached to a kidney of the patient; a method in which the obtained renal progenitor cells are suspended in physiological saline or the like to prepare a cell suspension, or the cells are subjected to three-dimensional culture (for example, Dev Cell. Sep. 11, 2012; 23(3): 637-651) to obtain a cell cluster, followed by directly transplanting the cell suspension or the cell cluster to a kidney of the patient; and a method in which three-dimensional culture is carried out on a scaffold constituted by Matrigel or the like, and the resulting renal progenitor cell cluster is transplanted. The site of transplantation is not limited as long as it is in a kidney. The site is preferably under the renal capsule. Examples of the kidney disease include acute renal damage, chronic renal failure, and chronic kidney diseases that have not progressed to chronic renal failure.

In the present invention, the number of the renal progenitor cells contained in the therapeutic agent for a kidney disease is not limited as long as the transplant can survive after the administration. The therapeutic agent may be prepared by with an increased or decreased number of cells depending on the size of the affected area, the size of the body, and/or the like.

EXAMPLES

The present invention is concretely described below based on Examples. However, the present invention is not limited to the following modes.

<1> Differentiation Induction from iPS Cells into Renal Progenitor Cells

Differentiation induction from iPS cells into renal progenitor cells was carried out according to the following protocol. As the iPS cells, 201B7-derived OSR1-GFP/SIX2-tdTomato reporter human iPS cells were used.

1. By accutase treatment, undifferentiated iPS cells were prepared into single cells, and the cells were suspended in ReproFF2 medium (ReproCELL) supplemented with 10 μM Y27632, followed by plating on wells coated with Matrigel (BD Biosciences) at a density of $1.0 \times 10^4$/well to $5.0 \times 10^4$/well, and then performing incubation for 24 hours at 37° C.

2. Twenty-four hours later (Day 1), medium replacement was carried out with a medium using DMEM/F12 Glutamax (Thermo Fisher Scientific Inc.) supplemented with vitamin A free B27 supplement (Thermo Fisher Scientific Inc.) as a basal medium, which medium is supplemented with 1 μM CHIR99021, 10 nM retinoic acid, 1 ng/ml BMP4, and 100 ng/ml FGF2 (preparation of a late posterior epiblast: step 1).

3. On Day 2, medium replacement was carried out with a medium using the same basal medium, which medium is supplemented with 3 μM CHIR99021, 1 ng/ml BMP7, and 100 ng/ml FGF2 (preparation of a mesodermal-lineage primitive streak: step 2).

4. On Day 3 and Day 4, medium replacement was carried out with a medium using the same basal medium, which medium is supplemented with 3 μM CHIR99021, 1 ng/ml BMP7, 100 ng/ml FGF2, and 10 μM A83-01 (preparation of a mesodermal-lineage late primitive streak: step 3).

5. On Day 5, Day 6, and Day 7, medium replacement was carried out with a medium using the same basal medium, which medium is supplemented with 3 μM CHIR99021, 1 ng/ml BMP7, 100 ng/ml FGF2, 10 ng/ml ACTIVIN, and 30 μM Y27632 (preparation of a metanephric-lineage late primitive streak: step 4).

6. On Day 8 and Day 9, medium replacement was carried out with a medium using the same basal medium, which medium is supplemented with 100 ng/ml FGF9 and 100 nM retinoic acid (preparation of a late posterior intermediate mesoderm: step 5).

7. On Day 10, Day 11, and Day 12, medium replacement was carried out with a medium using the same basal medium, which medium is supplemented with 10 ng/ml FGF9 and 1 μM CHIR99021 (preparation of renal progenitor cells: step 6).

The progress of the differentiation induction at each stage was confirmed based on expression of the markers described in Table 1.

Regarding the negative markers, the absence of their expression was confirmed. FIG. 1 shows the result of marker staining of cells at each stage. For the late posterior intermediate mesoderm and the renal progenitor cells, marker-positive cells were obtained at not less than 80%. A similar result was obtained when the medium in the above step 5 contained 200 ng/ml FGF9, 100 nM retinoic acid, and 25 ng/ml NOGGIN.

TABLE 1

| Marker genes in each stage | |
|---|---|
| Positive Marker | Negative Marker |
| ① CDX1, OCT4, NANOG, E-CDH | EOMES, BRACHYURY |
| ② BRACHYURY, CDX1 | OCT4, NANOG, E-CDH |
| ③ BRACHYURY, CDX2 | |
| ④ BRACHYURY, HOX11 | |
| ⑤ OSR1, HOX11, WT1 | |
| ⑥ OSR1, HOX11, WT1, SIX2, SALL1 | |

These results indicate that differentiation induction of renal progenitor cells from iPS cells could be achieved. The renal progenitor cells were obtained with a remarkably high differentiation induction efficiency of not less than 80%.

Figure 2:
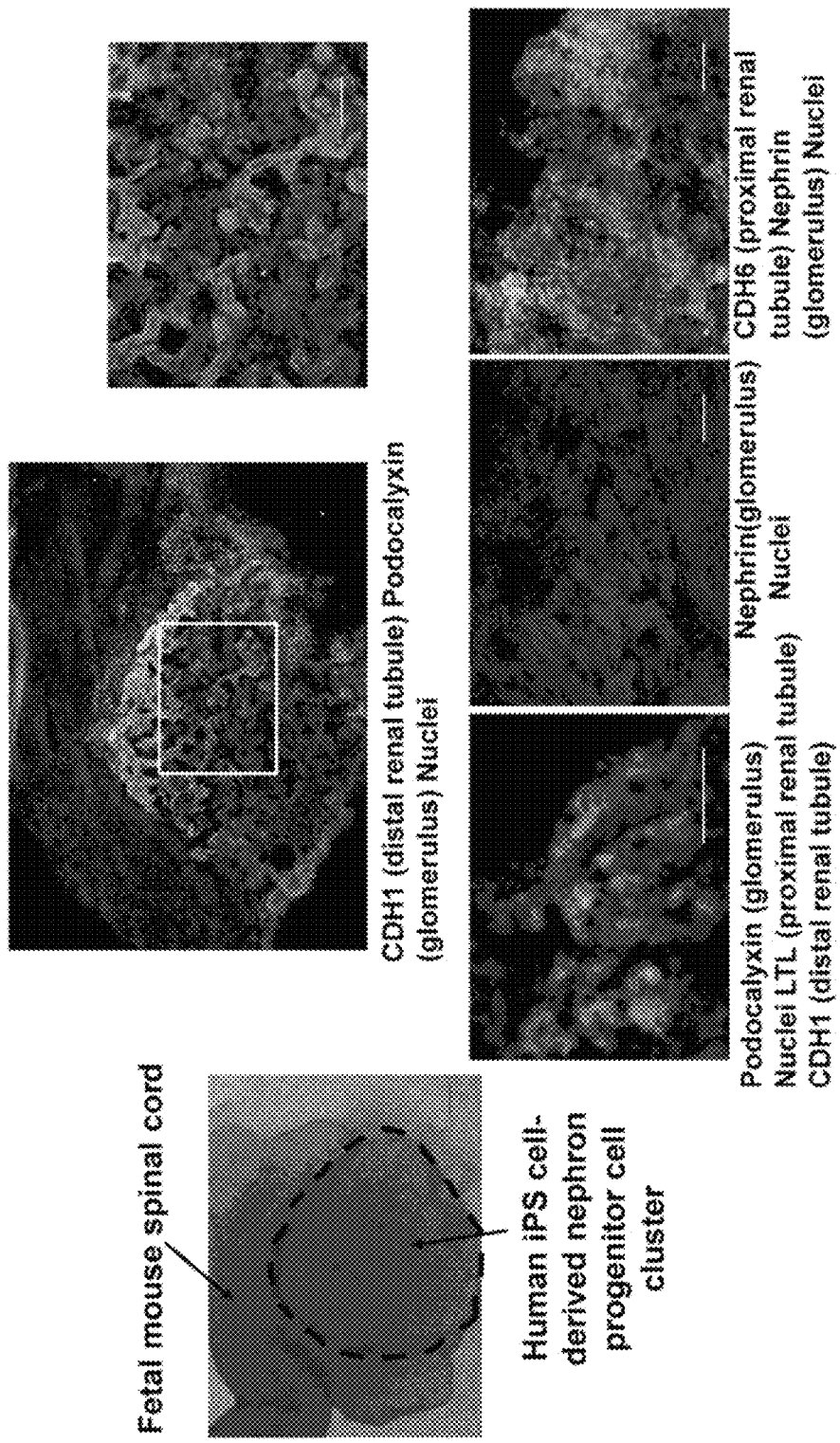
FIG. 2 shows photographs showing results of staining of a kidney organoid obtained by co-culture of renal progenitor cells derived from human iPS cells with mouse embryonic kidney. In the figure, Podocalyxin represents a marker of glomeruli; LTL represents a marker of proximal renal tubules; CDH1 represents a marker of distal renal tubules; CDH6 represents a marker of proximal renal tubules; and Nephrin represents a marker of glomeruli. Each scale bar represents 50 µm.

<2> Preparation of Kidney Organoid from Renal Progenitor Cells by Co-Culture with Fetal Mouse Kidney Cells The renal progenitor cells obtained in <1> were prepared into a cell cluster with a size of $1.0 \times 10^5$, and cultured in a basal medium supplemented with 1 µM CHIR99021 and 10 ng/ml FGF9 for 1 day. This was followed by co-culture with E11.5 fetal mouse spinal cord by semi-gas phase culture. As a result, as shown in FIG. 2, glomeruli and renal tubules were found. Thus, a kidney organoid could be successfully prepared.

<3> Preparation of Kidney Organoid by Culture of Renal Progenitor Cells Alone

Figure 3:
FIG. 3 shows photographs showing a bright field image and immunostaining images of kidney organoids obtained by culture of renal progenitor cells derived from human iPS cells. In the figure, Podocalyxin represents a marker of glomeruli; LTL represents a marker of proximal renal tubules; CDH1 and BRN1 represent markers of distal renal tubules and Henle's loop. *Dolichos biflorus* agglutinin (DBA) is a marker of distal renal tubules.
Figure 3:
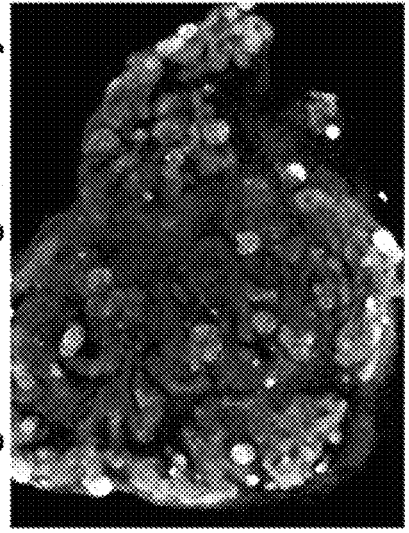
Figure 3:
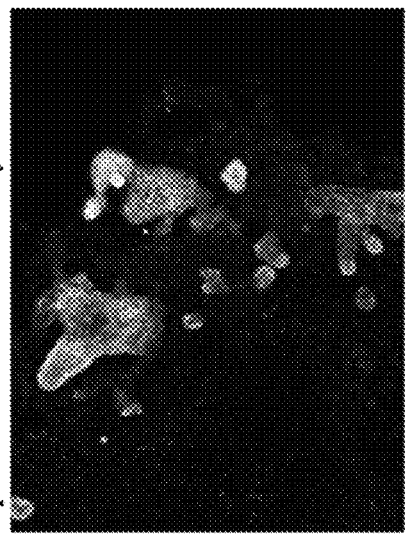

The renal progenitor cells obtained in <1> were prepared into a cell cluster with a size of $1.0 \times 10^5$, and cultured in a basal medium supplemented with 1 µM CHIR99021 and 200 ng/ml FGF9 for 1 or 2 days. The cell cluster was subjected to semi-gas phase culture in a basal medium supplemented with 5 µM CHIR99021 and 200 ng/ml FGF2 for 2 days, and then to semi-gas phase culture in the basal medium alone for 8 days. As a result, as shown in FIG. 3, glomeruli and renal tubules were found. Thus, a kidney organoid was successfully prepared. BRN1(+) CDH1(+) DBA(−) Henle's loop was also found.

What is claimed is:

1. A method of producing renal progenitor cells from intermediate mesodermal cells, the method consisting essentially of performing adherent culture of intermediate mesodermal cells in a medium comprising GSK (glycogen synthase kinase)-3β inhibitor and FGF (fibroblast growth factor) 9, with the proviso that the medium does not contain BMP inhibitor, to induce OSR1-positive/SIX2-positive renal progenitor cells from intermediate mesodermal cells with an efficiency of not less than 80%.

2. The method according to claim 1, wherein the intermediate mesodermal cells are OSR1-positive cells.

3. The method according to claim 1, wherein the GSK-3β inhibitor is CHIR99021.

4. The method according to claim 1, wherein the adherent culture is carried out using a culture vessel coated with an extracellular matrix.

5. The method according to claim 4, wherein the extracellular matrix is laminin 511 E8 fragment.

6. The method according to claim 1, wherein the intermediate mesodermal cells are intermediate mesodermal cells induced from pluripotent stem cells.

7. The method according to claim 1, wherein the medium consists essentially of the GSK (glycogen synthase kinase)-3β inhibitor and the FGF (fibroblast growth factor) 9 in a basal medium.

8. The method according to claim 7, wherein the basal medium is selected from the group consisting of IMDM, Medium 199, Eagle's Minimum Essential Medium (EMEM), αMEM, Dulbecco's modified Eagle's Medium (DMEM), Ham's F12 (F12) medium, RPMI 1640 medium, Fischer's medium, and mixed media thereof.

9. A method of producing renal progenitor cells, comprising performing adherent culture of intermediate mesodermal cells in a medium containing a GSK (glycogen synthase kinase)-3β inhibitor, a ROCK inhibitor and FGF (fibroblast growth factor) 9, to induce renal progenitor cells from intermediate mesodermal cells.

10. A method of producing renal progenitor cells from intermediate mesodermal cells, the method consisting essentially of performing adherent culture of intermediate mesodermal cells in a medium comprising GSK (glycogen synthase kinase)-3β inhibitor and FGF (fibroblast growth factor) 9, with the proviso that the medium does not contain BMP inhibitor, to induce OSR1-positive/SIX2-positive renal progenitor cells from intermediate mesodermal cells, wherein the intermediate mesodermal cells are intermediate mesodermal cells induced from pluripotent stem cells by a method comprising the following Steps (i) to (v):
   (i) a step of culturing pluripotent stem cells in a medium containing FGF2, BMP (bone morphogenetic protein) 4, a GSK-3β inhibitor, and retinoic acid or a derivative thereof;
   (ii) a step of culturing cells obtained in Step (i) in a medium containing FGF2, a GSK-3β inhibitor, and BMP7;
   (iii) a step of culturing cells obtained in Step (ii) in a medium containing FGF2, a GSK-3β inhibitor, BMP7, and a TGFβ inhibitor;
   (iv) a step of culturing cells obtained in Step (iii) in a medium containing FGF2, a GSK-3β inhibitor, BMP7, activin, and a ROCK inhibitor; and
   (v) a step of culturing cells obtained in Step (iv) in a medium containing retinoic acid or a derivative thereof, and FGF9.

11. The method according to claim 10, wherein the medium in Step (v) further contains a BMP inhibitor.

12. The method according to claim 10, wherein the pluripotent stem cells are induced pluripotent stem (iPS) cells.

13. The method according to claim 12, wherein the iPS cells are human iPS cells.

14. A method of producing renal progenitor cells from pluripotent stem cells, the method comprising the following Steps (i) to (vi):
   (i) a step of culturing pluripotent stem cells in a medium containing FGF2, BMP4, a GSK-3β inhibitor, and retinoic acid or a derivative thereof;
   (ii) a step of culturing cells obtained in Step (i) in a medium containing FGF2, a GSK-3β inhibitor, and BMP7;
   (iii) a step of culturing cells obtained in Step (ii) in a medium containing FGF2, a GSK-3β inhibitor, BMP7, and a TGFβ inhibitor;
   (iv) a step of culturing cells obtained in Step (iii) in a medium containing FGF2, a GSK-3β inhibitor, BMP7, activin, and a ROCK (Rho-kinase) inhibitor;
   (v) a step of culturing cells obtained in Step (iv) in a medium containing retinoic acid or a derivative thereof, and FGF9; and
   (vi) a step of culturing cells obtained in Step (v) in a medium containing a GSK-3β inhibitor and FGF9, to induce renal progenitor cells from intermediate mesodermal cells.

15. The method according to claim 14, wherein the medium in Step (v) further contains a BMP inhibitor.

16. The method according to claim 14, wherein the renal progenitor cells are SIX2-positive cells.

17. The method according to claim 14, wherein the cells obtained in Step (v) are OSR1-positive cells.

18. The method according to claim 14, wherein the medium in Step (vi) further contains a ROCK inhibitor.

19. The method according to claim 14, wherein the culture is carried out using a culture vessel coated with an extracellular matrix.

20. The method according to claim 19, wherein the extracellular matrix is laminin 511 E8 fragment.

21. The method according to claim 14, wherein the pluripotent stem cells are induced pluripotent stem (iPS) cells.

* * * * *